(12) United States Patent
DiMarco

(10) Patent No.: US 8,751,004 B2
(45) Date of Patent: Jun. 10, 2014

(54) BIPOLAR SPINAL CORD STIMULATION TO ACTIVATE THE EXPIRATORY MUSCLES TO RESTORE COUGH

(76) Inventor: Anthony Fortunato DiMarco, Solon, OH (US)

( * ) Notice: Subject to any disclaimer, the term of this patent is extended or adjusted under 35 U.S.C. 154(b) by 0 days.

(21) Appl. No.: 13/595,039

(22) Filed: Aug. 27, 2012

(65) Prior Publication Data

US 2014/0058490 A1   Feb. 27, 2014

(51) Int. Cl.
*A61N 1/05* (2006.01)

(52) U.S. Cl.
USPC ............................................. 607/42; 607/117

(58) Field of Classification Search
USPC ..................................... 607/2, 42, 43, 72, 73
See application file for complete search history.

(56) References Cited

U.S. PATENT DOCUMENTS

| | | | | |
|---|---|---|---|---|
| 5,999,855 A * | 12/1999 | DiMarco | ......................... | 607/42 |
| 6,233,488 B1 * | 5/2001 | Hess | ............................... | 607/58 |
| 7,840,270 B2 * | 11/2010 | Ignagni et al. | .................. | 607/42 |
| 8,352,036 B2 * | 1/2013 | DiMarco et al. | ................ | 607/42 |
| 8,406,885 B2 * | 3/2013 | Ignagni et al. | .................. | 607/42 |
| 2008/0051851 A1* | 2/2008 | Lin | ............................... | 607/42 |
| 2010/0010571 A1* | 1/2010 | Skelton et al. | .................. | 607/59 |

* cited by examiner

*Primary Examiner* — Brian T Gedeon
(74) *Attorney, Agent, or Firm* — Richard M. Klein; Fay Sharpe LLP

(57) ABSTRACT

Methods and devices are provided for electrical stimulation of the expiratory muscles in humans or other mammals to produce cough in patients with spinal cord injuries resulting in paralysis of the expiratory muscles. An electrode, or a group of two or more electrodes (i.e. wire lead electrodes, disc electrodes, etc.) are positioned along the spinal cord, usually along the dorsal epidural surface. The electrodes can be located at different spinal cord levels and can be located in a parallel arrangement. Electrical stimulation, such as bipolar electrical stimulation, is then applied to activate the expiratory muscles and produce cough.

29 Claims, 12 Drawing Sheets

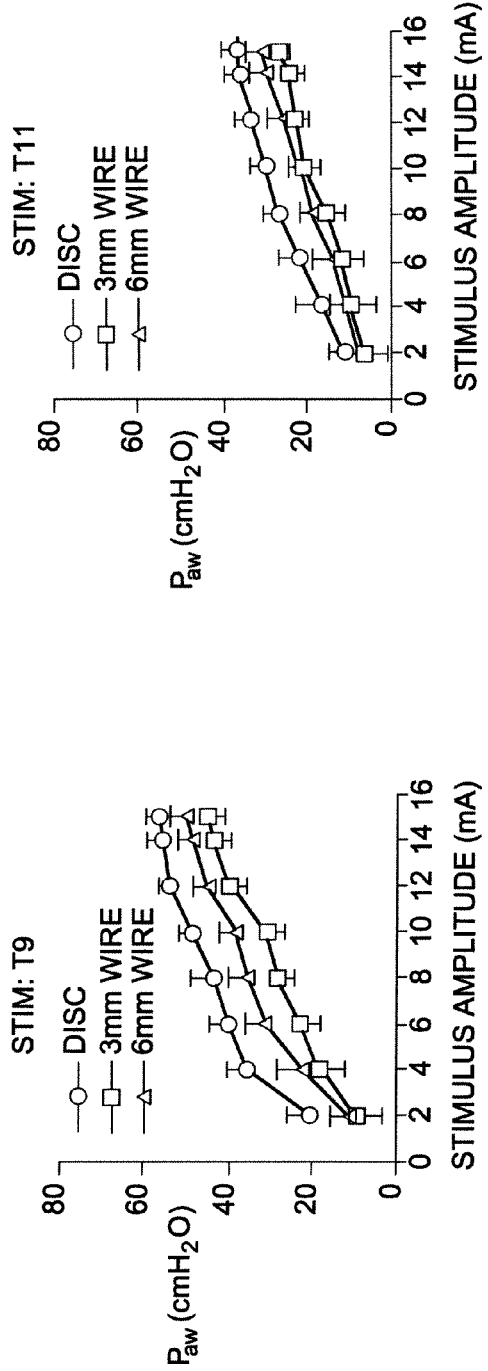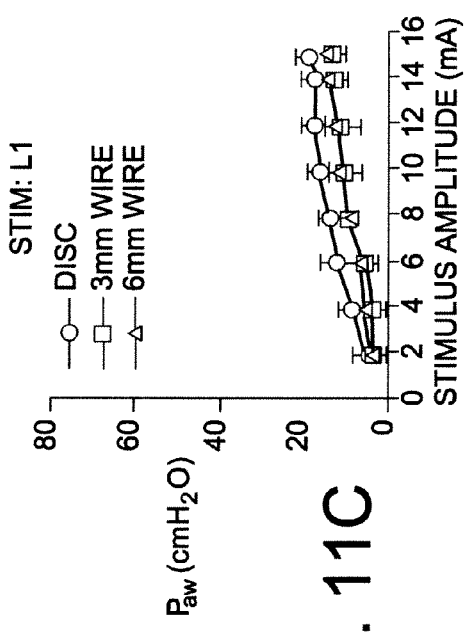

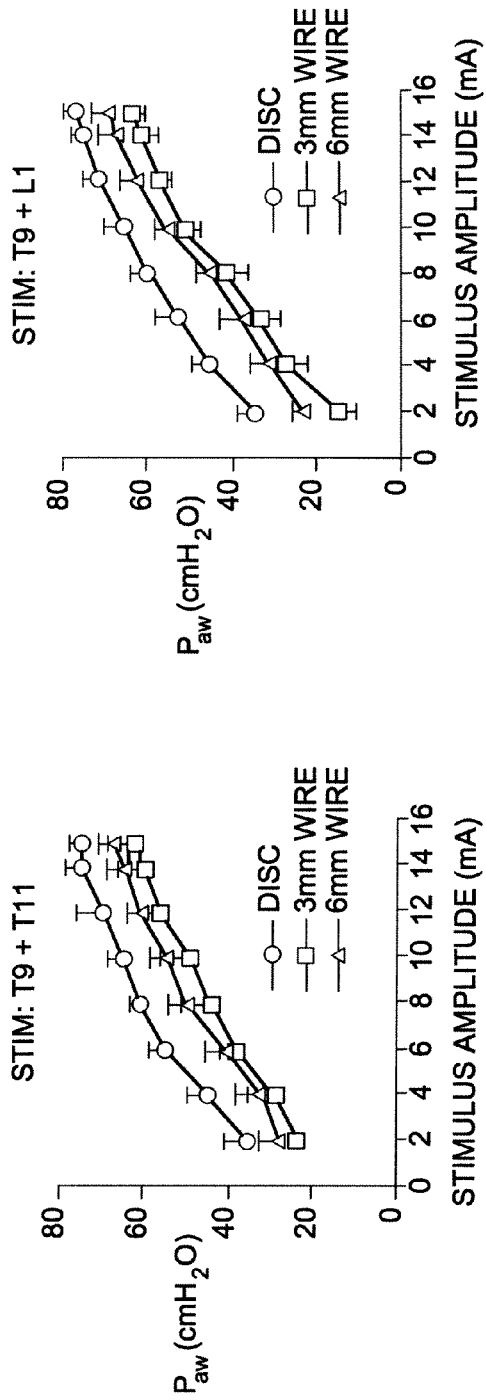
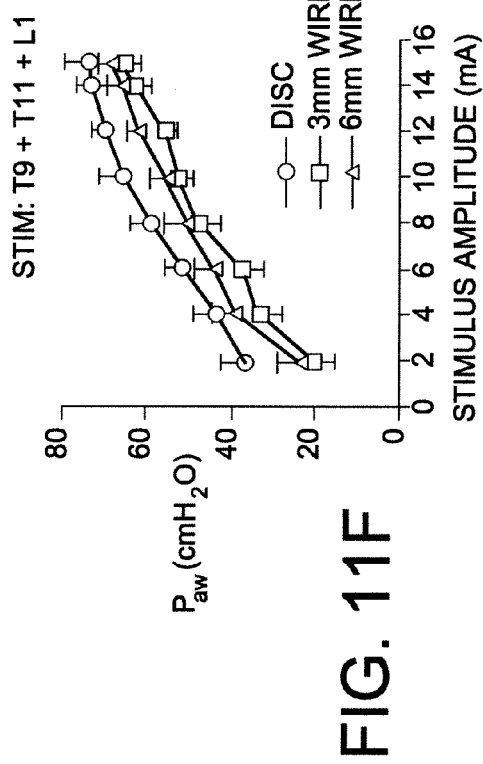
FIG. 11D
FIG. 11E
FIG. 11F

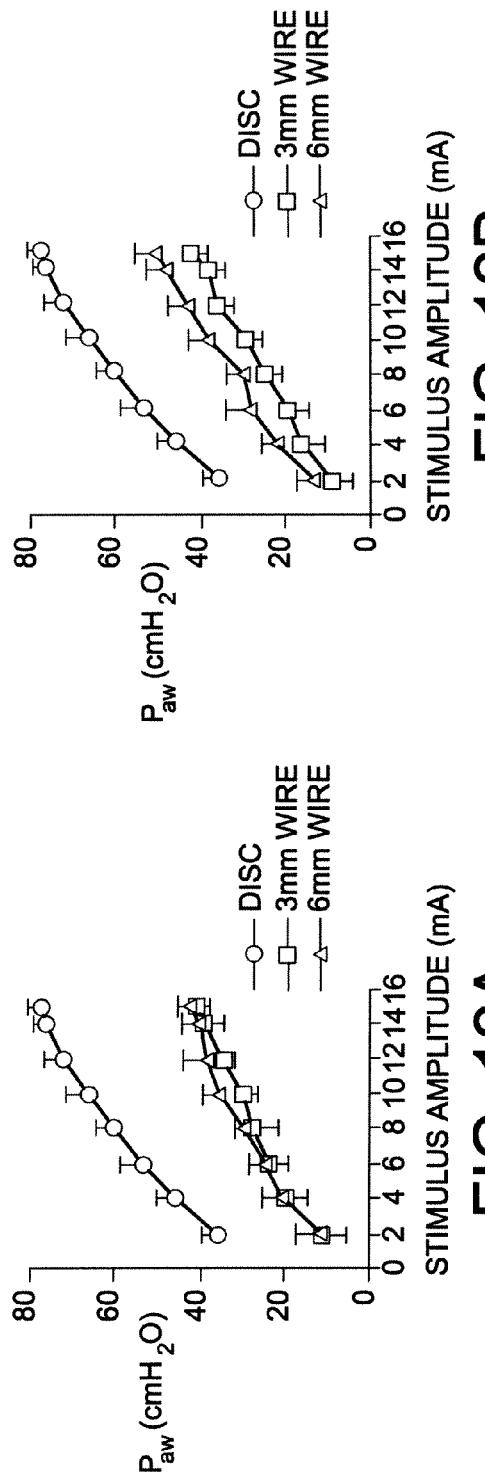
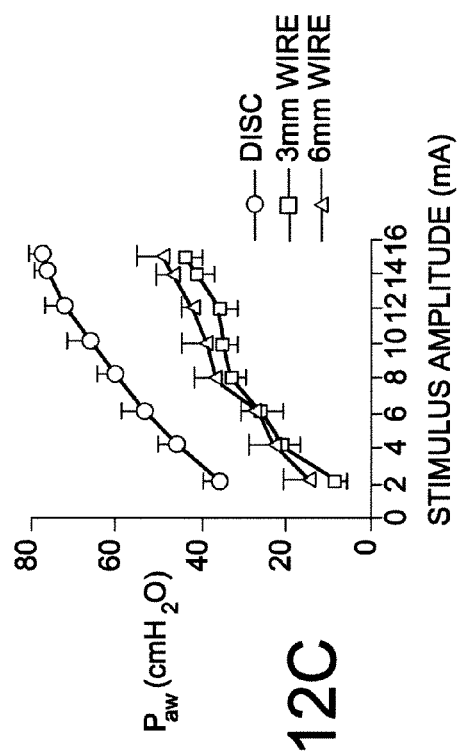
FIG. 12A
FIG. 12B
FIG. 12C

BIPOLAR SPINAL CORD STIMULATION TO ACTIVATE THE EXPIRATORY MUSCLES TO RESTORE COUGH

BACKGROUND

The present disclosure relates to methods and systems for electrical stimulation of the expiratory muscles to produce cough in human patients or other mammals with spinal cord injuries resulting in the paralysis of their expiratory muscles.

The sequence of cough is divided into four phases: inspiration, compression, expiration and cessation. During inspiration, a variable amount of air is inhaled. The greater the amount of air inhaled, the larger the force that can be developed by the expiratory muscles. As lung volume increases, the expiratory muscles progressively improve in their pre-contractile length. During compression, the glottis closes followed by expiratory muscle contraction. When the expiratory muscles contract against a closed glottis, intrathoracic and intraabdominal pressures become quite high and may exceed 200 $cmH_2O$. When pleural pressure increases, lung volume decreases as the intrathoracic gases are compressed. The glottis usually remains closed for about 200 milliseconds (msec). The opening of the glottis signals the onset of the expiratory phase of cough. This is an active process associated with passive oscillations of tissue and gas. These oscillations cause the noise generally characteristic of cough. Following glottic opening, intrathoracic pressure drops rapidly toward atmospheric levels, whereas the pressure at the alveolar level remains positive and actually continues to rise for a short while. The high intraalveolar pressures simultaneously promote high expiratory flow rates and tend to collapse central airways. Accordingly, the transient peaks of expiratory flow noted during cough represent both the sum of the flow related to the displaced volumes of gas in the central airways which are dynamically collapsed and also the flow of gas from the distal parenchymal units passing through these collapsing airways. These transient peaks play an important role in the movement of foreign material toward the airway opening. The final phase of cough is characterized by the relaxation of the expiratory muscles and the antagonistic activity of the diaphragm and other inspiratory muscles and the return to normal breathing.

Patients with spinal cord injuries involving the T5 level or higher suffer from paralysis of their expiratory muscles, including the lower intercostal and abdominal muscles, which are the major muscles for the development of an effective cough. There are about 250,000 patients with spinal cord injury in the United States, with about 12,000 new injuries occurring each year. Within this group, about 40 to about 50 percent of these patients have cervical spinal cord lesions resulting in tetraplegia. Following spinal cord injury (SCI), respiratory complications account for most of the morbidity and mortality in this patient population.

Despite intensive respiratory management, these patients frequently develop atelectasis (lung collapse), bronchitis and pneumonia. In epidemiological studies of over 5,000 patients sustaining SCI, the leading cause of death was pneumonia. The development of respiratory complications in this patient group is directly related to their inability to cough and clear secretions. The lack of an adequate cough defense system occurs as a consequence of paralysis of virtually all of their expiratory muscles. Although ciliary activity is an important mechanism of mucus clearance, coughing is necessary when the cilia are ineffective in removing secretions or overwhelmed by excessive secretions.

Strokes also account for 5 million deaths a year worldwide; 30% of patients with stroke die within 3 months. Most deaths are caused by stroke-related complications, of which respiratory tract infections are the most common. Absent or weak voluntary cough in stroke patients has been associated with a higher incidence of aspiration and respiratory infections. Restoration of an effective cough and associated reduction in incidence of respiratory infections would substantially decrease death rates after stroke.

Currently employed techniques to manage airway secretions include patient positioning, active suctioning, manual assistance by abdominal compression (assisted cough) and/or use of a mechanical insufflation-exsufflation device.

Patient positioning places the patient in relatively awkward positions for prolonged periods to remove secretions by gravity, and is quite uncomfortable. In active suctioning, a suction catheter is repeatedly introduced into the lower respiratory tract. This method is uncomfortable and can result in tracheal injury, irritation, hemoptysis, and respiratory tract infections. This method also does not facilitate removal of secretions from small airways where they are produced and often results in gas exchange abnormalities. With regard to assisted cough and the mechanical insufflation-exsufflation device, these techniques do not result in uniform distribution of pressure within the intrathoracic cavity and, therefore, have limited effectiveness in many patients. Another major disadvantage of these methods is that they require the presence of trained personnel, and thus are time-consuming, costly, and labor-intensive.

Functional electrical stimulation of the expiratory muscles has the potential to provide a normal and effective cough mechanism. There are three methods by which the expiratory muscles can be activated to produce cough: (1) high frequency magnetic stimulation; (2) surface abdominal muscle stimulation; and (3) lower thoracic spinal cord stimulation (SCS).

Magnetic stimulation is an experimental device which can be applied to the lower back to activate the neural pathways innervating the expiratory muscles. In normal subjects, this technique has been shown to result in the generation of large positive airway pressures and expiratory flow rates. One major advantage of this technique is that it can be applied non-invasively. However, several disadvantages are also present. Initially, airway pressures and airflow rates produced during magnetic stimulation are not significantly different from that which could be generated during maximal spontaneous efforts, and can be quite low. Next, this device requires the application of current applied at high stimulus frequencies (>20 Hz), which generates substantial heat at the stimulating coil and consequently carries the risk of thermal injury. In addition, this device is quite large, requires an external power source, and is not very portable. This is a substantial disadvantage since patients can still be mobile and cough is often required on an emergent basis. Fourth, large amounts of adipose tissue (common in patients with SCI) may preclude successful stimulation in obese patients. Finally, the presence of a trained caregiver is still required to properly apply the device.

Direct stimulation of the abdominal muscles with electrodes positioned over the surface of the abdominal wall has been tried. In several previous animal and human studies, increases in positive airway pressure were marginal in the range of ~30 $cmH_2O$. In some studies, employing surface electrodes with much larger surface areas, pressure generation was quite substantial in the range of 150 $cmH_2O$. As with magnetic stimulation, this method also has the advantage of being non-invasive. However, the repeated application of electrodes over the skin may lead to thermal injury, irritation, and breakdown. Also, significant adipose tissue may interfere with its successful application in obese patients due to the high electrical resistance of fatty tissue. Repeated application of electrodes to the skin surface may also prove to be quite tedious and cumbersome.

Lower thoracic spinal cord stimulation (SCS) currently involves the use of disc-shaped or paddle-shaped leads, which are essentially a two-dimensional substrate with an electrode on one side. Such leads are typically installed, repositioned, or removed using one or more laminectomies, which is a major invasive surgery in which portions of the vertebral bone are removed and which can take four to six hours and require two to three days of hospital admission. In addition, the leads can be difficult to position accurately and the leads can change position.

Many patients find the current technology, which involves an invasive procedure, acceptable given the potential benefits. However, it would be desirable to provide additional methods that could be less invasive.

BRIEF DESCRIPTION

The present disclosure thus relates to methods, devices and systems for using electrical stimulation, such as unipolar and/or bipolar stimulation, of the expiratory muscles of a patient to produce cough. Very generally, an electrode, or a group of two or more electrodes, is inserted along the lower thoracic region of the spinal cord of the patient. The electrodes are spaced apart from each other longitudinally in the midline or in a parallel arrangement (each just lateral to the midline) at different spinal cord levels. An effective amount of electrical stimulation, such as unipolar and/or bipolar stimulation, is applied using the electrodes to cause the expiratory muscles to produce cough.

Disclosed in various embodiments is a method of electrically activating expiratory muscles of a patient to produce cough, comprising: applying stimulation using a first wire lead and a second wire lead to activate the expiratory muscles of the patient to produce cough; wherein the first wire lead and the second wire lead are located in a substantially parallel arrangement along a spinal cord of the patient, the first wire lead and the second wire lead each contain a first electrode and a second electrode, the first electrodes of the first wire lead and the second wire lead are located at a first spinal cord level, and the second electrodes of the first wire lead and the second wire lead are located at a second spinal cord level.

In some embodiments, the first electrodes and the second electrodes all act as cathodes, and unipolar stimulation is applied.

In other embodiments, the first electrodes act as cathodes and the second electrodes act as anodes, and bipolar stimulation is applied. Sometimes, the cathodes are closer to the brain of the patient than the anodes.

The unipolar or bipolar stimulation can be applied at a frequency of 10 Hz to 1000 Hz; a voltage of 10 V to 50 V; a pulse amplitude of 1 mA to 40 mA; with a pulse width of 10 microseconds to 10 seconds; or at a maximum charge density of 1.0 microCoulombs/mm$^2$. In specific embodiments, the unipolar or bipolar stimulation is applied at a pulse amplitude of 10 mA to 40 mA and a pulse width of 200 μsec to 400 μsec.

The first wire lead and the second wire lead may be located on a dorsal epidural surface of the spinal cord. The first wire lead and the second wire lead can be located parallel to the midline of the patient.

Sometimes, the first spinal cord level is the T9 spinal cord level and the second spinal cord level is the T11 spinal cord level. Alternatively, the first spinal cord level is the T11 spinal cord level and the second spinal cord level is the L1 spinal cord level. As another option, the first spinal cord level is the T9 spinal cord level and the second spinal cord level is the L1 spinal cord level.

Also disclosed herein in various embodiments is a method of electrically activating expiratory muscles of a patient to produce cough, comprising: applying bipolar stimulation using a first wire lead and a second wire lead to activate the expiratory muscles of the patient to produce cough; wherein the first wire lead and the second wire lead are located in a substantially longitudinal arrangement along a spinal cord of the patient, the first wire lead and the second wire lead each contain a first electrode and a second electrode, the first electrode of the first wire lead is located at a first spinal cord level, the second electrode of the first wire lead is located at a second spinal cord level, the first electrode of the second wire lead is located at a third spinal cord level, and the second electrode of the second wire lead is located at a fourth spinal cord level.

Sometimes, the first electrode of the first wire lead acts as a cathode, the second electrode of the first wire lead acts as an anode, the first electrode of the second wire lead acts as a cathode, and the second electrode of the second wire lead acts as an anode.

In other embodiments, the first electrode of the first wire lead acts as a cathode and the second electrode of the second wire lead acts as an anode. The other electrodes may or may not be used.

The bipolar stimulation can be applied at a pulse amplitude of 1 mA to 40 mA, or at a maximum charge density of 1.0 microCoulombs/mm$^2$. In particular embodiments, the bipolar stimulation is applied at a pulse amplitude of 10 mA to 40 mA; and a pulse width of 200 μsec to 400 μsec.

Also disclosed in various embodiments is a method of electrically activating expiratory muscles in a patient to produce cough, comprising: positioning two or more electrodes along the surface of the lower thoracic regions of the spinal cord of a patient, wherein the electrodes are located in a parallel arrangement at the same or different spinal cord levels; and applying an effective amount of bipolar electrical stimulation to the expiratory muscles by means of the electrodes to produce cough.

The bipolar stimulation can be applied at a frequency of 10 Hz to 1000 Hz, or at a voltage of 10 V to 50 V, or at a pulse amplitude of 1 mA to 40 mA, or with a pulse width of 10 microseconds to 10 seconds, or at a maximum charge density of 1.0 microCoulombs/mm$^2$. Sometimes, the bipolar stimulation is applied at a pulse amplitude of 10 mA to 40 mA; and a pulse width of 200 μsec to 400 μsec.

The electrodes can be located on a dorsal epidural surface of the spinal cord. The electrodes may be located parallel to a midline of the patient.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 4 is a series of illustrations (i.e.

FIG. 8 is a set of graphs (i.e.

FIG. 10 is a set of graphs (i.e.

FIG. 11 is a set of graphs (i.e. FIGS. 11A-11F) showing airway pressure vs. stimulus amplitude for three different electrode systems with unipolar stimulation and different electrode combinations.

FIG. 12 is a set of graphs (i.e. FIGS. 12A-12C) showing the airway pressure vs. stimulus amplitude for longitudinal wire leads as arranged in FIG. 4.

DETAILED DESCRIPTION

Figure 1:
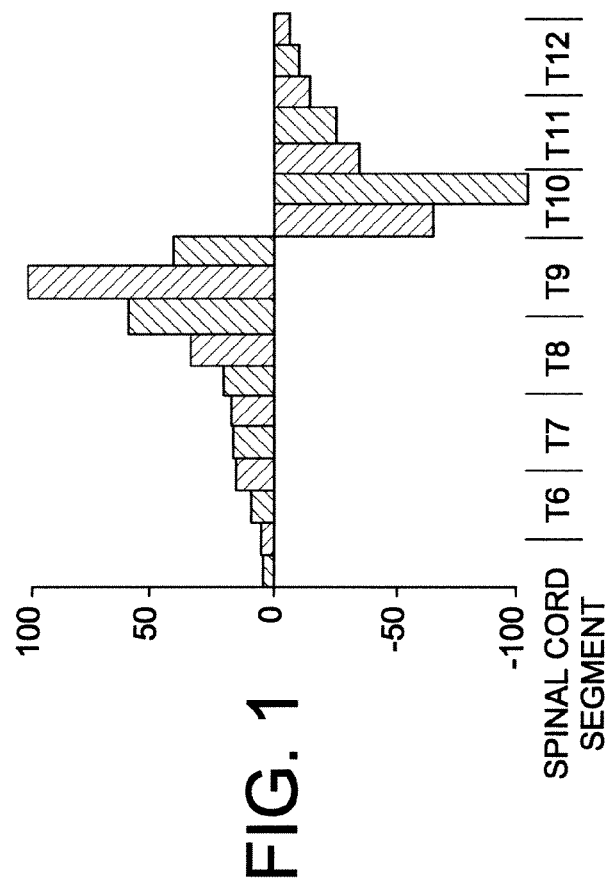
FIG. 1 is a graph showing the pattern of current spread around the spinal cord from an electrode.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range of "from about 2 to about 10" also discloses the range "from 2 to 10."

The human spinal cord is divided into the cervical, thoracic, lumbar, sacral, and coccygeal spinal cord levels. The term "spinal cord level" is used herein to refer to a location or point where spinal roots emanate from the spinal cord. Such locations are associated with a vertebra, and are denoted herein with reference to the particular vertebrae, for example the "T9 spinal cord level". The thoracic region includes twelve levels numbered T1-T12, of which T5-T12 are lower thoracic levels. With injury between T5-T12, loss of expiratory muscle function and, consequently, cough may occur.

The present disclosure relates to the use of lower thoracic spinal cord stimulation (SCS) to activate the abdominal and internal intercostal muscles of patients who are unable to activate these muscles themselves. The goal of SCS is to generate large positive airway pressures and high peak flow rates in such patients, into the range sufficient to produce an effective cough. The present devices are portable and likely to be effective in all patients, even obese individuals. Generally, two or more electrodes (i.e. wire lead electrodes, disc electrodes, etc.) are implanted along the spinal cord of a patient. The electrodes are located either in the midline with a single electrode spaced longitudinally at different spinal levels or multiple electrodes in a parallel arrangement at one or more spinal cord levels. Bipolar stimulation is then applied to these electrodes (i.e. wire lead electrodes, disc electrodes, etc.) to activate the expiratory muscles to produce cough.

Unipolar or monopolar stimulation refers to the stimulating electrodes having the same polarity (i.e. negative) and having the same magnitude relative to a ground. Current does not flow between the stimulating electrodes, or if so only a leakage current.

Bipolar stimulation refers to the electrodes having different polarities (i.e. one is negative, one is positive) relative to each other. Put another way, one of the electrodes can be considered the ground, whereas in unipolar stimulation a remote electrode, distant from the field of stimulation, is needed to serve as the ground. The difference between unipolar stimulation and bipolar stimulation is that in bipolar stimulation, current also runs between the stimulating electrodes, i.e. along the spinal cord, and thus provides more localized stimulation.

In specific embodiments, optimal activation of the expiratory muscles can be achieved with bipolar stimulation using a single wire lead in the midline with electrodes spaced at different spinal levels, disc electrodes placed in the midline or two percutaneous wire leads placed in a parallel arrangement. This unique arrangement and type of stimulation results in the generation of positive airway pressures (one measure of an effective cough mechanism) similar to that achieved with unipolar disc/paddle leads. In addition, the positioning of the electrodes in closer proximity to spinal roots (as would occur with parallel wire leads) may result in a greater degree of expiratory muscle activation for a given charge density.

One major advantage is that wire lead electrodes, compared to disc electrodes, can be placed much less invasively on an out-patient basis. They can be easily placed in an optimal position as well. In this regard, a significant limitation of disc or paddle leads is the requirement of an invasive procedure to accomplish electrode placement. The placement of 4 mm disc electrodes requires multiple hemi-laminotomies (laminotomy and laminectomy refer to the same procedure) over the lower thoracic spine. While straightforward, this procedure requires general anesthesia and prolonged operative time, in the range of 4-6 hours depending upon body habitus, degree of scoliosis, and other anatomic factors. As a consequence, there are some (small) risks associated with this procedure including discomfort, infection, and bleeding. Wire lead placement is associated with shorter surgery times, less blood loss, smaller surgical incisions, shorter length of hospital stay, and faster recovery times. This should lead to greater acceptance of such devices for purposes of prophylaxis against potential complications, and improve patient quality of life and health.

The spinal cord stimulation devices and methods described herein activate the expiratory muscles primarily by ventral root stimulation, which requires high levels of current. As explained above, the bipolar stimulation causes current to run along the spinal cord. In comparison, some current pain control devices stimulate only the dorsal columns at low current levels.

Bipolar stimulation permits current to spread external to the spinal cord as well as within the spinal cord. The spread of current external to the spinal cord can directly activate the motor roots of the spinal cord. The spread of current within the spinal cord can stimulate and activate dorsal column pathways. Experiments have been performed to determine the pattern of current spread around the spinal cord. Using recording electrodes both above and below the area of stimulation (T9 level), the electric field was determined over the ventral surface of the spinal cord. Stimulation was performed with single shocks (0.5 millisecond duration, 1.0 milliAmpere amplitude). Long pulses are necessary to achieve a steady state field and avoid artifacts. Measurements were taken every 0.5-1.0 cm in the rostral-caudal direction. The value of the electric field ($E=-\Delta V/\Delta X$) was determined by dividing the measured electrical potential difference ($\Delta V$) by the distance between the electrode wires ($\Delta X=0.5$ cm). The ground was positioned cephalad to the stimulating electrode, accounting for the asymmetric distribution of the electric field with larger values on the rostral compared to the caudal site. As shown in FIG. 1, there is an exponential decrease in the magnitude of the electric field as a function of distance from the stimulating electrode. Within 6 cm of the stimulating electrode, the magnitude of the electric field fell to values below 5%. Based upon the measured threshold values, this data provides the stimulus current values necessary for direct ventral root activation. These results are consistent with measured EMG values during stimulation at various points along the lower thoracic spinal cord in animal studies, indicating that the spread of current falls off rapidly beyond 2 spinal cord segments rostral and caudal to the stimulating electrode.

Figure 2:
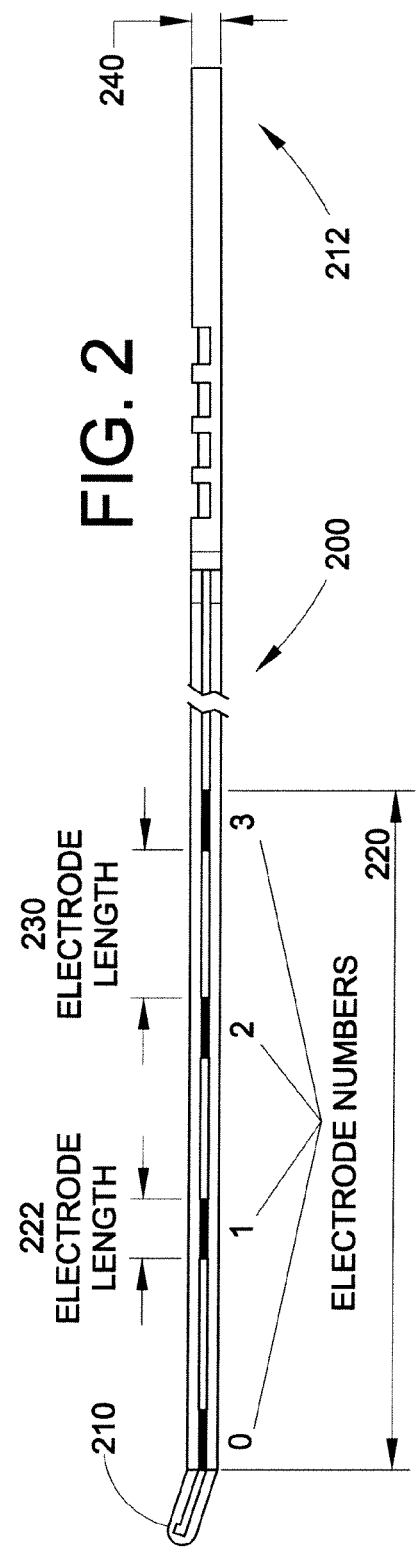
FIG. 2 is a diagram of a percutaneous wire lead containing at least two electrodes.

One or more percutaneous wire leads are implanted along the spinal cord of the patient, i.e. in the rostral-caudal direction. An exemplary wire lead 200 is illustrated in FIG. 2. The wire lead includes a distal end 210 and a proximal end 212. At least two electrodes 220 are located along the wire lead, usually at the distal end. As depicted here, the wire lead has four such electrodes (numbered 0, 1, 2, 3). Each electrode has an electrode length 222, with a spacing length 230 between adjacent electrodes. The proximal end is used for connecting the wire lead to an electrical stimulator. The wire lead has a diameter 240.

Two different wire leads are specifically used in the present disclosure, although others may be used as appropriate. One wire lead is referred to as a "3 mm lead". In this lead, the diameter of the wire lead is 1.3 mm and the electrode length is 3 mm, so that the surface area of each electrode is about 12.2 mm². The 3 mm lead has a total of eight electrodes and a total length of 66 mm. The other wire lead is referred to as a "6 mm lead". This lead has a diameter of 1.3 mm and an electrode length of 6 mm, so that the surface area of each electrode is about 24.5 mm². The 6 mm lead has a total of four electrodes and a total length of 60 mm. Such wire leads are commercially available from, for example, Medtronic, offered as the Pisces Quad Compact™ or Pisces Quad Plus™ wire leads.

Figure 3:
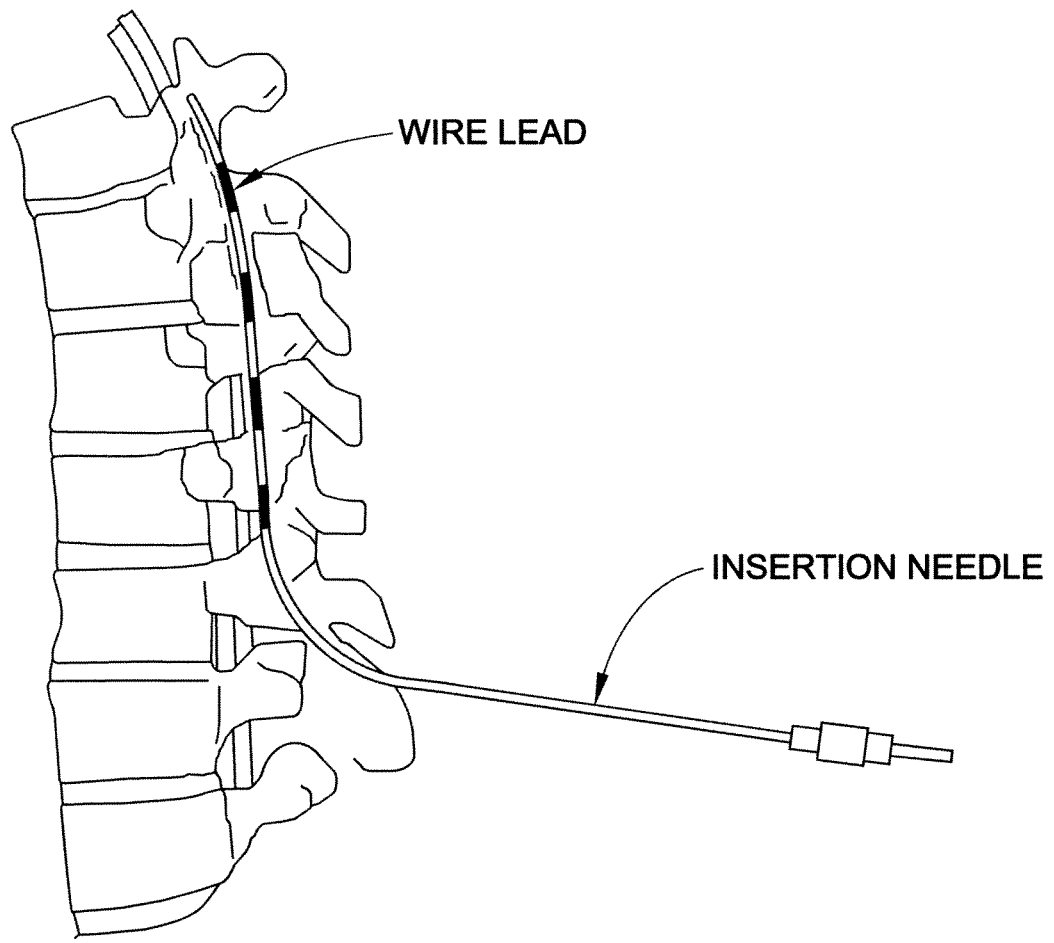
FIG. 3 is an illustration of a percutaneous wire lead being inserted using a minimally invasive technique. The electrode will be located on the dorsal epidural surface of the spinal cord.

As illustrated in FIG. 3, the one or more wire leads are implanted on a dorsal epidural surface of the spinal cord. When two leads are used, they are placed in parallel positions within the dorsal epidural space. This can be done using minimally invasive techniques, for example using an insertion needle through an incision of 1 to 1.5 cm in size. There is no need to expose a large surface area, as is usually needed to insert disc/paddle leads.

Figure 4A:
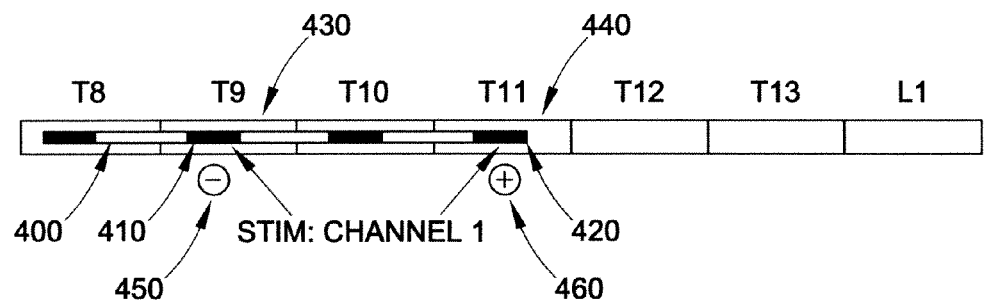
FIGS. 4A, 4B and 4C) showing three different arrangements of wire leads positioned longitudinally to each other for bipolar stimulation.

Two different arrangements of wire leads are contemplated. In both arrangements, the wire leads are implanted so that the electrodes are located at different spinal cord levels. FIG. 4 shows wire leads (positioned in the midline) which are located longitudinally relative to each other. FIG. 5 shows two wire leads which are located parallel relative to each other and just lateral to the midline of the body.

Generally, a first wire lead 400 is placed along the spinal cord (not shown). The first wire lead 400 has a first electrode 410 and a second electrode 420. The first electrode 410 is located at a first spinal cord level 430, and the second electrode 420 is located at a second spinal cord level 440. The first spinal cord level 430 and the second spinal cord level 440 are different. When bipolar stimulation is applied, the first electrode acts as a cathode 450 and the second electrode acts as an anode 460. FIG. 4A illustrates an embodiment in which only one wire lead is implanted and used as described.

In some embodiments, the first spinal cord level is the T9 spinal cord level and the second spinal cord level is the T11 spinal cord level. In other embodiments, the first spinal cord level is the T11 spinal cord level and the second spinal cord level is the L1 spinal cord level. In yet other embodiments, the first spinal cord level is the T9 spinal cord level and the second spinal cord level is the L1 spinal cord level.

A second wire lead 500 may also be placed along the spinal cord of the patient. Again, the second wire lead has a first electrode 510 and a second electrode 520. The first electrode 510 of the second wire lead is located at a third spinal cord level 530, and the second electrode 520 of the second wire lead is located at a fourth spinal cord level 540.

Figure 4B:
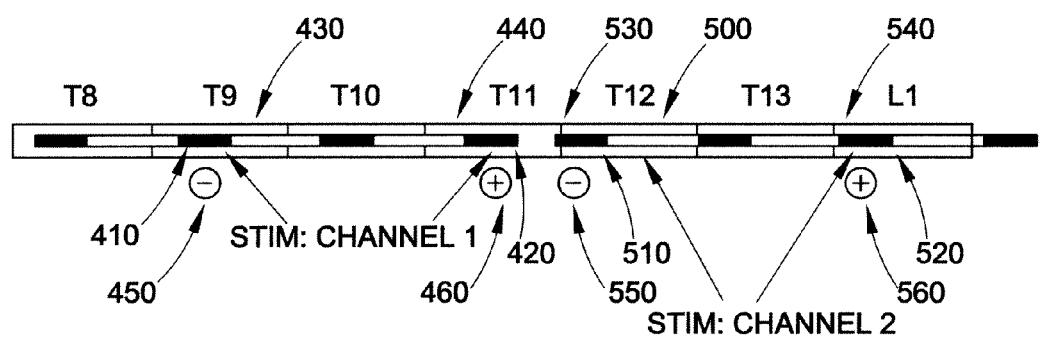
Figure 4C:
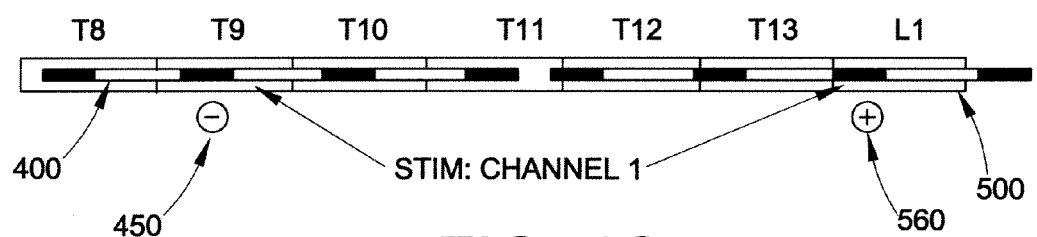
Figure 5:
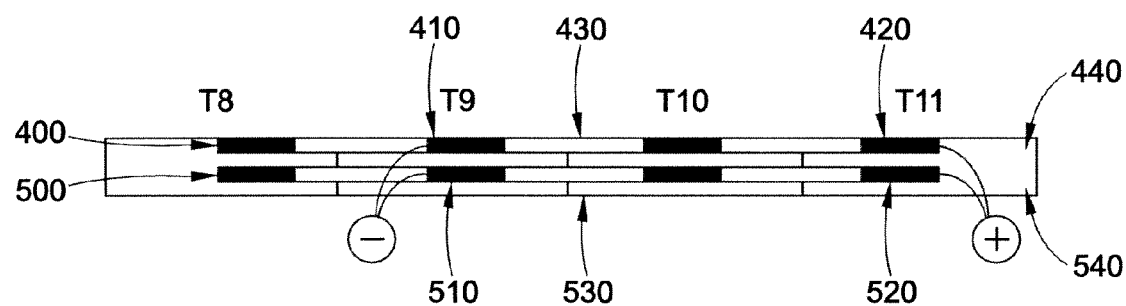
FIG. 5 is an illustration showing two wire leads positioned in a parallel arrangement relative to each other for bipolar stimulation.

In the embodiments illustrated in FIG. 4B and FIG. 4C, where a first wire lead and a second wire lead are arranged longitudinally, the second electrode of the first wire lead and the first electrode of the second wire lead are located at different spinal cord positions but in some instances may be located in similar spinal cord regions such as T11, as shown. The first electrode of the first wire lead and the second electrode of the second wire lead are located at different spinal cord levels. In particular embodiments, the second electrode of the first wire lead and the first electrode of the second wire lead may both be located at the T11 spinal cord level or at different spinal levels.

In some instances, the first electrode 410 of the first wire lead acts as a cathode 450, the second electrode 420 of the first wire lead acts as an anode 460, the first electrode 510 of the second wire lead acts as a cathode 550, and the second electrode 520 of the second wire lead acts as an anode 560. This arrangement could be useful, for example, for electrical stimulation at the T9, T11, and L1 spinal cord levels (i.e. three different levels). See FIG. 4B.

Alternatively, two longitudinal wire leads may be used because an individual wire lead is of insufficient length to bridge different spinal cord levels which are desired to be stimulated. For example, one of the electrodes of the first wire lead 400 could act as a cathode 450, and one of the electrodes of the second wire lead 500 could act as an anode 560. In this instance, the other electrodes on the first wire lead and the second wire lead would not be used for stimulation. See FIG. 4C.

In the embodiment illustrated in FIG. 5, where the first wire lead 400 and the second wire lead 500 are arranged in parallel, the first spinal cord level 430 is the same as the third spinal cord level 530, and the second spinal cord level 440 is the same as the fourth spinal cord level 540. Put another way, the first and second wire leads are arranged at the same spinal cord levels and are both parallel to the midline of the body. Usually, they are placed just lateral to the midline of the spinal cord. The first electrodes 410, 510 of the first and second wire leads can be connected in parallel to function as a common electrode. Similarly, the second electrodes 420, 520 of the first and second wire leads can be connected in parallel to function as a common electrode.

Bipolar stimulation with two wire leads arranged in parallel is believed to have several advantages. First, a high degree of expiratory muscle activation is achieved. Secondly, this arrangement has the potential of being associated with fewer side effects because the pattern of current distribution is more localized. Finally, the parallel wire arrangement has been associated with a much lower incidence of migration of the wire leads.

In all embodiments described herein, the cathode is desirably closer to the brain of the patient than the anode (i.e. the cathode is rostral compared to the anode).

The wire leads are then connected to an electrical stimulator. The stimulator sends electrical signals to the wire leads to activate the electrodes and the expiratory muscles. The stimulator generally has a wide range of stimulus parameters, such as voltage output, pulse duration (i.e. stimulus duration), and stimulus frequency. An exemplary stimulator is the S88 dual output square wave pulse stimulator available from the Grass Division of Astro-Med Inc. (West Warwick, R.I.).

It should be noted that although a ground is not needed for bipolar stimulation, in some embodiments a third electrode may be connected to the electrical stimulator to act as a ground. This can allow unipolar stimulation to be applied in appropriate circumstances using the same implanted device. The ground may be positioned in a pocket over the paraspinal muscles.

Figure 6:
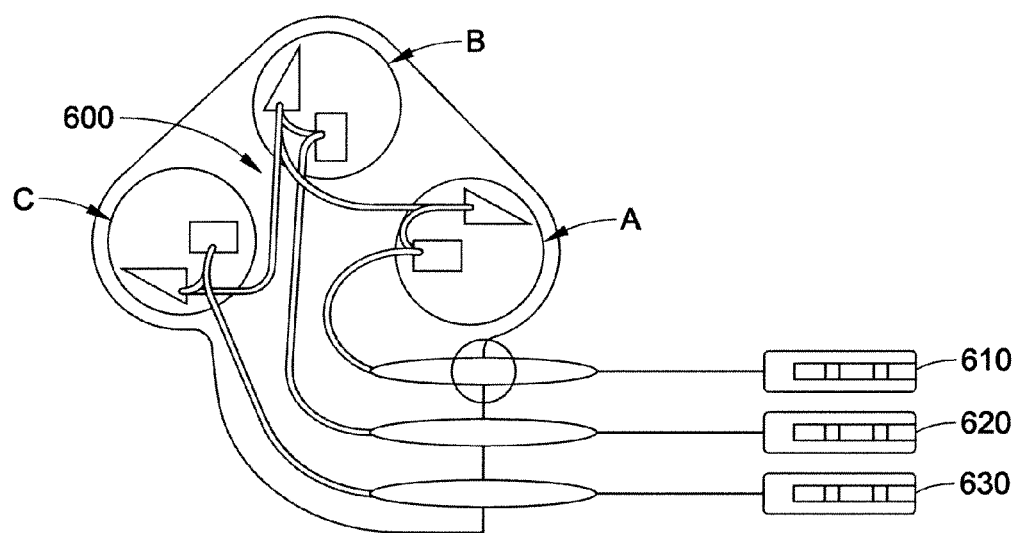
FIG. 6 is an illustration of an electrical stimulator to which the wire leads are connected.

An example of a suitable implantable receiver stimulator is illustrated in FIG. 6. The depicted device 600 is a three channel device having three passive receivers (one for each channel), which are powered by near inductive radiofrequency fields from a transmitter (not shown) located outside the body. The amplitude of each channel can be independently controlled. Connectors lead from each channel to the first wire lead 610, second wire lead 620, and optional ground 630. The stimulator is comparable in size to cardiac pacemakers and other implantable stimulation devices. As illustrated here, channels A and B would be used in combination to provide bipolar stimulation. Channel C would be used to provide unipolar stimulation. The stimulator can generate a single charge balanced biphasic stimulus pulse for each command issued by the external transmitter. The stimulator includes a capacitor (not shown) that operates such that any malfunction which results in the transmitter being continuously 'on' does not cause the electrodes (of the wire leads) to pass a continuous direct current. The mechanisms of the implantable stimulator and the external transmitter are substantially similar to those described in U.S. Pat. No. 5,911,218, the disclosure of which is entirely incorporated by reference herein.

The maximum charge the stimulator is expected to deliver is 8 µC (200 µsec and 40 mA). Thus, the maximum charge density expected on a single electrode is 0.33 µC/mm². This is within the generally accepted safe limits of 1.0 µC/mm² for tissue damage and 3.0 µC/mm² for corrosion of electrodes. A significant safety margin is present due to the intermittent nature of the applied stimulation.

In embodiments, the bipolar stimulation may be applied at a frequency of 10 Hz to 1000 Hz; a voltage of 10 V to 50 V; a pulse amplitude of 1 mA to 40 mA; and/or a pulse width of 10 µsec to 10 seconds. The stimulation is usually a square waveform. In particular embodiments, the stimulus frequency is greater than 50 Hz. Ideally, the stimulation is able to generate a large positive airway pressure of at least 60 cmH$_2$O and a peak airflow rate of at least 270 L/min (4.5 L/sec), which are characteristic of an effective cough. In more particular embodiments, the bipolar stimulation may be applied at a frequency of 40 Hz to 53 Hz; a voltage of 10 V to 40 V; a pulse amplitude of 10 mA to 40 mA; and/or a pulse width of 200 µsec to 400 µsec. Patients with stroke may still have intact sensation, which would limit the amplitude of any stimulation. However, the duration of stimulation is very brief (0.4 to 0.6 seconds), and the stimulus current can be reduced further by increasing stimulus frequency to achieve comparable expiratory muscle activation. A higher stimulus frequency and a lower current will result in less pain fiber stimulation.

In desirable embodiments, the wire leads are used to stimulate the T9 and T11 spinal cord levels. Stimulation at the L1 level can result in undesirable leg movement in some individuals.

The following examples are for purposes of further illustrating the present disclosure. The examples are merely illustrative and are not intended to limit the methods or devices made in accordance with the disclosure to the materials, conditions, or process parameters set forth therein.

EXAMPLES

Dog Trials with Disc Electrodes

In previous animal studies in dogs using a single disc electrode, it was found that maximum expiratory airway pressures occurred with stimulation applied in the T9-T10 spinal cord region. Stimulation above and below this region resulted in progressive reductions in airway pressure generation as the electrode was positioned either more caudally or rostrally. Employing a stimulus frequency of 50 Hz, airway pressure generation rose progressively with increasing stimulus amplitude until a plateau was reached at about 15 millamperes (mA). Increases in stimulus frequency also resulted in progressive increases in pressure generation until a plateau was reached between 30 and 40 Hz. Pressure generation was highly reproducible as the coefficient of variance was found to be less than 10% in each animal.

In subsequent studies, it was determined that dorsal stimulation was more effective than ventral stimulation. For any given stimulus current applied, airway pressure generation was higher with the application of stimulation on the dorsal surface compared to the ventral surface of the spinal cord.

It was also previously determined that the mechanism of expiratory muscle activation during stimulation at the 19 level involved stimulation of spinal cord pathways. Direct motor root activation was also an important mechanism of expiratory muscle activation.

Combined stimulation with a first electrode at the T9/T10 level and a second electrode at the T13/L1 level resulted in significantly greater pressure generation in the range of 150-200 cmH$_2$O at total lung capacity (TLC). However, using more than 2 electrodes did not result in further increases in pressure generation.

To summarize, optimal activation requires dorsal placement of two electrodes at the T19 and T13/L1 levels.

First Set of Dog Trials with Wire Leads

Acute animal studies on anesthetized dogs were performed in which wire leads were directly compared with disc electrodes.

The disc electrode was a disc having a diameter of 4 mm and made of 90% platinum/10% iridium embedded in a polyester reinforced silicone elastomer apron with a diameter of 0.470 inches. These electrodes are commercially available as the Resume Model 3586 from Medtronic or the Atrostim Model TF-3-3-U from Atrotech. The disc electrode had a total surface area of 12.6 mm$^2$.

Two wire leads were used. The first wire lead is referred to as a "3 mm lead", and was a Medtronic Pisces Quad Compact™ wire lead. The diameter of this wire lead is 1.3 mm and the electrode length is 3 mm, so that the surface area of each electrode is about 12.2 mm$^2$. The 3 mm lead has a total of eight electrodes and a total length of 66 mm. The second wire lead is referred to as a "6 mm lead", and was a Medtronic Pisces Plus™ wire lead. This lead has a diameter of 1.3 mm and an electrode length of 6 mm, so that the surface area of each electrode is about 24.5 mm$^2$. The 6 mm lead has a total of four electrodes and a total length of 60 mm. Each of these wire electrodes had sufficient length to span the T9 thru T11 spinal cord segments.

All animals were anesthetized with pentobarbital sodium (25 mg/kg) given intravenously. Anesthetic level was maintained with supplemental doses of pentobarbital sodium (1-2 mg/kg), as needed. A large bore cuffed endotracheal tube was placed directly into the trachea in the mid-cervical region and sutured in place. A small catheter was positioned in the femoral vein to provide supplemental anesthesia and administer fluids. A separate catheter was placed in the femoral artery to monitor blood pressure. A heating blanket (Harvard Apparatus, Cambridge, Mass., USA) was used to maintain body temperature at 38±0.5° C. End-tidal PCO$_2$ was monitored continuously at the tracheal opening with a rapidly responding CO$_2$ analyzer (DRE Inc., Louisville, Ky., USA). A differential pressure transducer (Validyne, MP45, Northridge, Calif., USA) was used to measure airway pressure at the airway opening. Airway pressure was always measured under conditions of airway occlusion at functional residual capacity (FRC). Peak airflow rate was measured following release of occlusion with a pneumotachograph (Hans Rudolph, Kansas City, Mo.). Stimulation was applied over a range of stimulus amplitudes (50 Hz, pulse width 0.2 msec) until a plateau in pressure generation was achieved. When a remote ground was employed, a 1 cm disc electrode was implanted in the back musculature. Since cough is a ballistic maneuver requiring high pressure and airflow rate development, and patients generally employed maximum settings in our clinical trial, our focus was on maximum airway pressure and peak airflow rate development in these studies. Studies were performed in 6 animals.

Experiment #1

Unipolar Stimulation

Figure 9:
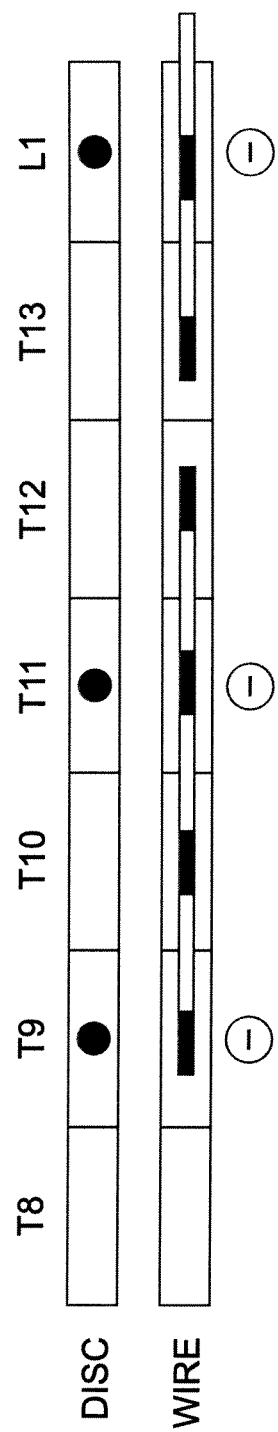
FIG. 9 is an illustration showing wire leads positioned longitudinally to each other for unipolar stimulation.

The wire leads or disc electrodes were positioned in the midline (unipolar stimulation). A graphical illustration is shown in FIG. 9.

Figure 10A:
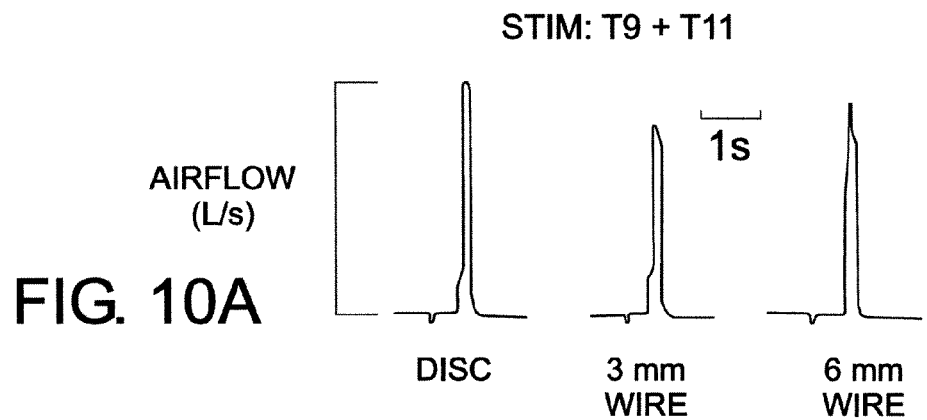
FIGS. 10A and 10B) showing airway pressure and peak airflow for three different electrode systems (i.e. disc electrodes, 3 mm wire leads and 6 mm wire leads) with unipolar stimulation.
Figure 10B:
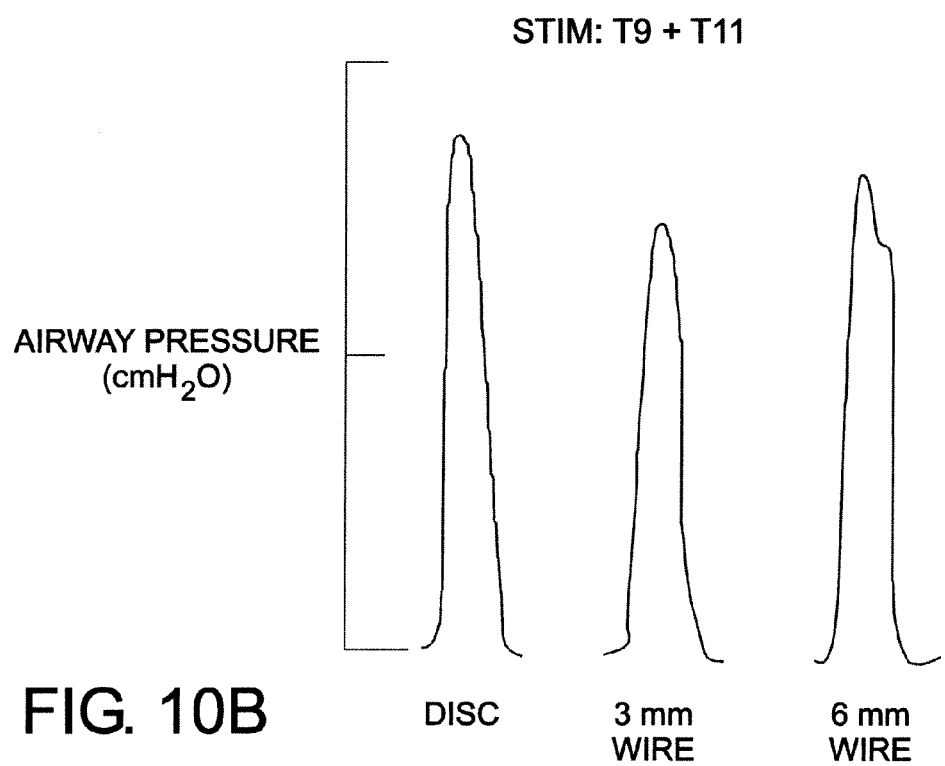

The effects of maximum combined SCS at the T9+T11 spinal levels on airway pressure and peak airflow development with each of the 3 electrode systems are shown for one animal in FIG. 10. Similar airway pressure and peak airflow rate development were achieved for each system.

FIG. 11 is a set of graphs showing airway pressure generation (P$_{aw}$, cmH$_2$O) vs. stimulus amplitude (mA) for each electrode type and combinations of spinal cord level stimulation. Table 1 below shows the peak airflow rate (in L/s) and peak P$_{aw}$ (in cmH$_2$O) for the electrode types and combinations of spinal cord level stimulation.

TABLE 1

| Unipolar Stimulation | | | | | | | | |
| --- | --- | --- | --- | --- | --- | --- | --- | --- |
| T9 | Peak Flow | P$_{aw}$ | T11 | Peak Flow | P$_{aw}$ | L1 | Peak Flow | P$_{aw}$ |
| Disc | 2.9 ± 0.2 | 56 ± 3 | Disc | 2.6 ± 0.1 | 37 ± 4 | Disc | 1.1 ± 0.1 | 20 ± 4 |
| 3 mm | 2.3 ± 0.1* | 45 ± 4* | 3 mm | 1.8 ± 0.2* | 27 ± 3* | 3 mm | 0.8 ± 0.1 | 14 ± 3 |
| 6 mm | 2.6 ± 0.1 | 49 ± 4 | 6 mm | 2.2 ± 0.1 | 31 ± 5 | 6 mm | 1.0 ± 0.1 | 16 ± 3 |
| T9 + T11 | Peak Flow | P$_{aw}$ | T9 + L1 | Peak Flow | P$_{aw}$ | T9 + T11 + L1 | Peak Flow | P$_{aw}$ |
| Disc | 3.9 ± 0.2 | 75 ± 3 | Disc | 4.0 ± 0.2 | 77 ± 3 | Disc | 3.8 ± 0.2 | 74 ± 6 |
| 3 mm | 3.0 ± 0.1* | 62 ± 6* | 3 mm | 3.2 ± 0.1* | 64 ± 3* | 3 mm | 3.2 ± 0.1* | 65 ± 3 |
| 6 mm | 3.4 ± 0.2 | 67 ± 4 | 6 mm | 3.6 ± 0.1 | 70 ± 4 | 6 mm | 3.5 ± 0.1 | 69 ± 4 |

*P < 0.05 as compared to the disc electrode

With each electrode type, there were progressive increases in pressure development with increasing stimulus current until a plateau was reached between 14-15 mA. Use of both the 3 mm and 6 mm wire leads generally resulted in smaller airway pressures and peak air flow rates compared to the disc electrode. Pressure generation with the 6 mm wire lead was somewhat greater than the 3 mm wire lead.

With combined stimulation with 2 electrodes, maximum airway pressure and flow rates with the 3 mm wire were significantly smaller than that achieved with the disc electrode (p<0.05). Combined stimulation with 3 electrode combinations (regardless of electrode type) did not result in significantly greater airway pressure or peak flow generation compared to use of 2 electrodes. Stimulation with the 3 mm and 6 mm wire leads resulted in about 80% and about 90%, respectively, of the maximum airway pressures and peak airflow rates generated with the disc electrodes. The 6 mm wire lead offered a small advantage compared to the 3 mm wire lead, which is believed to be due to the larger surface area of the electrode (25.5 mm$^2$ vs. 12.3 mm$^2$).

Experiment #2

Longitudinal Wire Leads, Bipolar Stimulation

The wire leads could be used for bipolar stimulation. A bipolar stimulation system would not require surgical placement of the anode. The span of each wire lead (66 and 60 mm for the 3 mm and 6 mm wire leads, respectively) allowed for bipolar stimulation between the T9-T11 and T11-L1 spinal levels. Use of two longitudinally placed wire leads allowed for bipolar stimulation between the T9-L1 spinal levels. Three different wire lead arrangements are displayed in FIG. 4. In the arrangements marked B and C, two wire leads are longitudinally arranged relative to each other. In arrangement B, four electrodes are stimulated (T9+T11+L1), whereas in arrangement C only two electrodes are stimulated (T9+L1).

As with unipolar stimulation, bipolar stimulation resulted in progressive increases in airway pressure generation until a plateau was reached between 14 and 15 mA. Airway pressure generation as a function of stimulus amplitude (50 Hz, 0.2 msec pulse duration) with bipolar stimulation is shown in FIG. 12, labeled A/B/C corresponding to the wire lead arrangement of FIG. 4. All three wire lead configurations were compared to the unipolar stimulation using disc electrodes for T9+L1 from Experiment #1. Table 2 below shows the peak airflow rate (in L/s) and peak $P_{aw}$ (in $cmH_2O$) for the electrode types and combinations of spinal cord level stimulation.

TABLE 2

Longitudinal Leads, Bipolar Stimulation

| A | Peak Flow | $P_{aw}$ | B | Peak Flow | $P_{aw}$ | C | Peak Flow | $P_{aw}$ |
|---|---|---|---|---|---|---|---|---|
| Disc | 4.0 ± 0.2 | 77 ± 3 | Disc | 4.0 ± 0.2 | 77 ± 3 | Disc | 4.0 ± 0.2 | 77 ± 3 |
| 3 mm | 2.2 ± 0.2* | 40 ± 4* | 3 mm | 2.2 ± 0.1* | 42 ± 4* | 3 mm | 2.3 ± 0.2* | 44 ± 4* |
| 6 mm | 2.3 ± 0.1* | 42 ± 3 | 6 mm | 2.7 ± 0.1 | 50 ± 5* | 6 mm | 2.6 ± 0.1* | 49 ± 6* |

*P < 0.05 as compared to the disc electrode

Pressure generation with each wire lead configuration resulted in substantially smaller airway pressure generation at each level of current (p<0.05). While the 6 mm wire lead resulted in somewhat greater pressures compared to the 3 mm wire lead, the differences were not significant.

Maximum airway pressure and peak airway flow generation are shown in the table. With the 3 mm and 6 mm leads, maximum airway and peak airflow rates were ~55 and ~65% of that achieved with the disc electrodes, respectively. These results emphasize the importance of a remote ground in achieving a broad electrical field to achieve more complete expiratory muscle activation with a midline electrode design.

Experiment #3

Parallel Wire Leads, Bipolar Stimulation

One of the major mechanisms by which the expiratory muscles are activated through spinal cord stimulation (SCS) is via direct motor root stimulation. Electrode positioning in closer proximity to the spinal roots therefore may result in a greater degree of expiratory muscle activation for a given charge density. The placement of a side by side wire lead electrode arrangement, with each electrode positioned parallel to the midline, was thus evaluated. This wire lead arrangement is displayed in FIG. 5.

Figure 13:
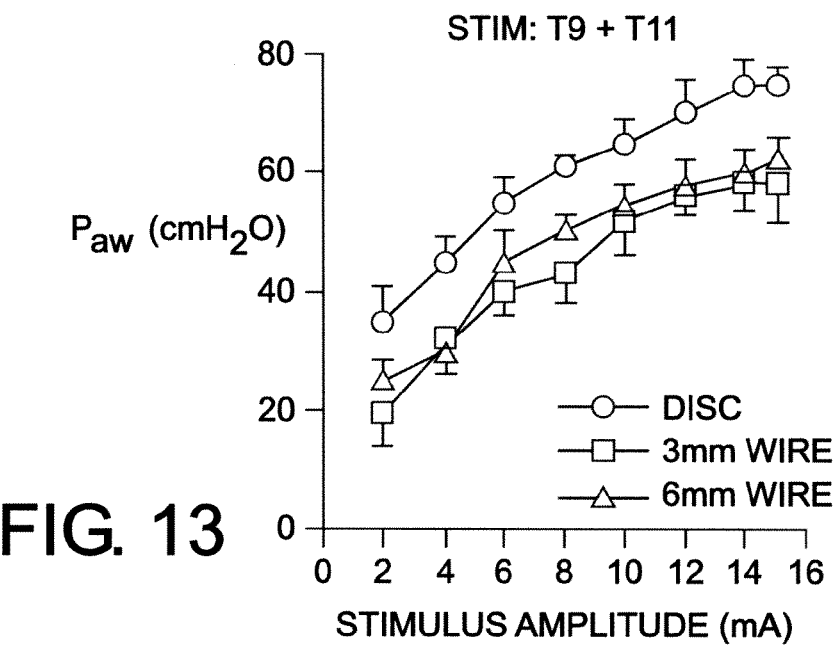
FIG. 13 is a graph showing the airway pressure vs. stimulus amplitude for lateral wire leads with bipolar stimulation.

Airway pressure generation as a function of stimulus amplitude (50 Hz, 0.2 msec pulse duration) with bipolar stimulation is shown in FIG. 13. This wire lead configuration was compared to the unipolar stimulation using disc electrodes for T9+T11 from Experiment #1 in Table 3 below.

TABLE 3

Parallel Leads, Bipolar Stimulation

| T9 + T11 | Peak Flow | $P_{aw}$ |
|---|---|---|
| Disc | 3.9 ± 0.2 | 75 ± 3 |
| 3 mm | 3.0 ± 0.2* | 58 ± 6* |
| 6 mm | 3.1 ± 0.1* | 62 ± 4* |

*P < 0.05 as compared to the disc electrode

With increasing stimulus current, there were progressive increases in airway pressure generation. While there were no significant differences between the 3 and 6 mm leads, the maximum pressures generated with the wire electrodes were significantly smaller than that achieved with the disc electrodes (p<0.05). With the 3 and 6 mm leads, maximum airway pressures and peak airflow rates were about 77 and about 80%, respectively, that of the disc electrodes. These results are comparable to that achieved with the wire leads in Experiment #1.

Experiment #4

Parallel Wire Leads, Unipolar Stimulation

Figure 14:
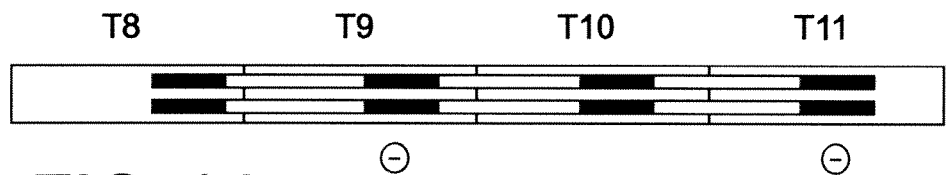
FIG. 14 is an illustration showing wire leads positioned parallel to each other for unipolar stimulation.

The wire leads here were placed as in Experiment #3, except that each of the electrodes at the T9 level were connected in parallel and functioned as a common cathode. Similarly, each of the electrodes at the T11 level were connected in parallel and functioned as a second common cathode. A remote ground was used. This wire lead arrangement is displayed in FIG. 14.

Figure 15:
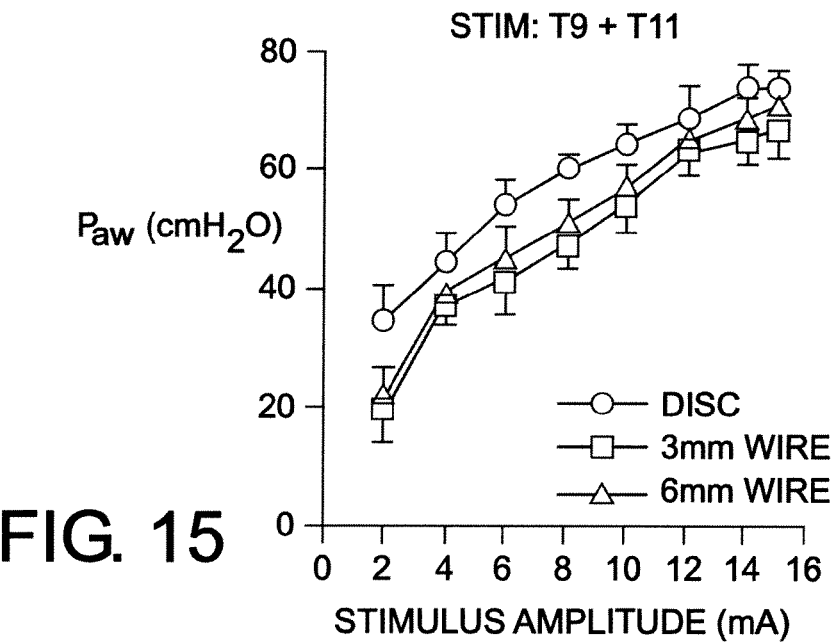
FIG. 15 is a graph showing the airway pressure vs. stimulus amplitude for parallel wire leads with unipolar stimulation.

Airway pressure generation as a function of stimulus amplitude with unipolar stimulation is shown in FIG. 15. This wire lead configuration was compared to the unipolar stimulation using disc electrodes for T9+T11 from Experiment #1 in Table 4 below.

TABLE 4

Parallel Leads, Unipolar Stimulation

| T9 + T11 | Peak Flow | $P_{aw}$ |
|---|---|---|
| Disc | 3.9 ± 0.2 | 75 ± 3 |
| 3 mm | 3.4 ± 0.2 | 68 ± 5 |
| 6 mm | 3.8 ± 0.1 | 72 ± 4 |

There were no significant differences in maximum airway pressure and peak airflow generation between each of the wire leads (see the table). During maximum stimulation with the 3 and 6 mm wire leads, airway pressure and peak airflow rate generation were about 90% and about 97% of that achieved with the disc electrodes for T9+T11 from Experiment #1.

Human Trials with Disc Electrodes

Figure 7:
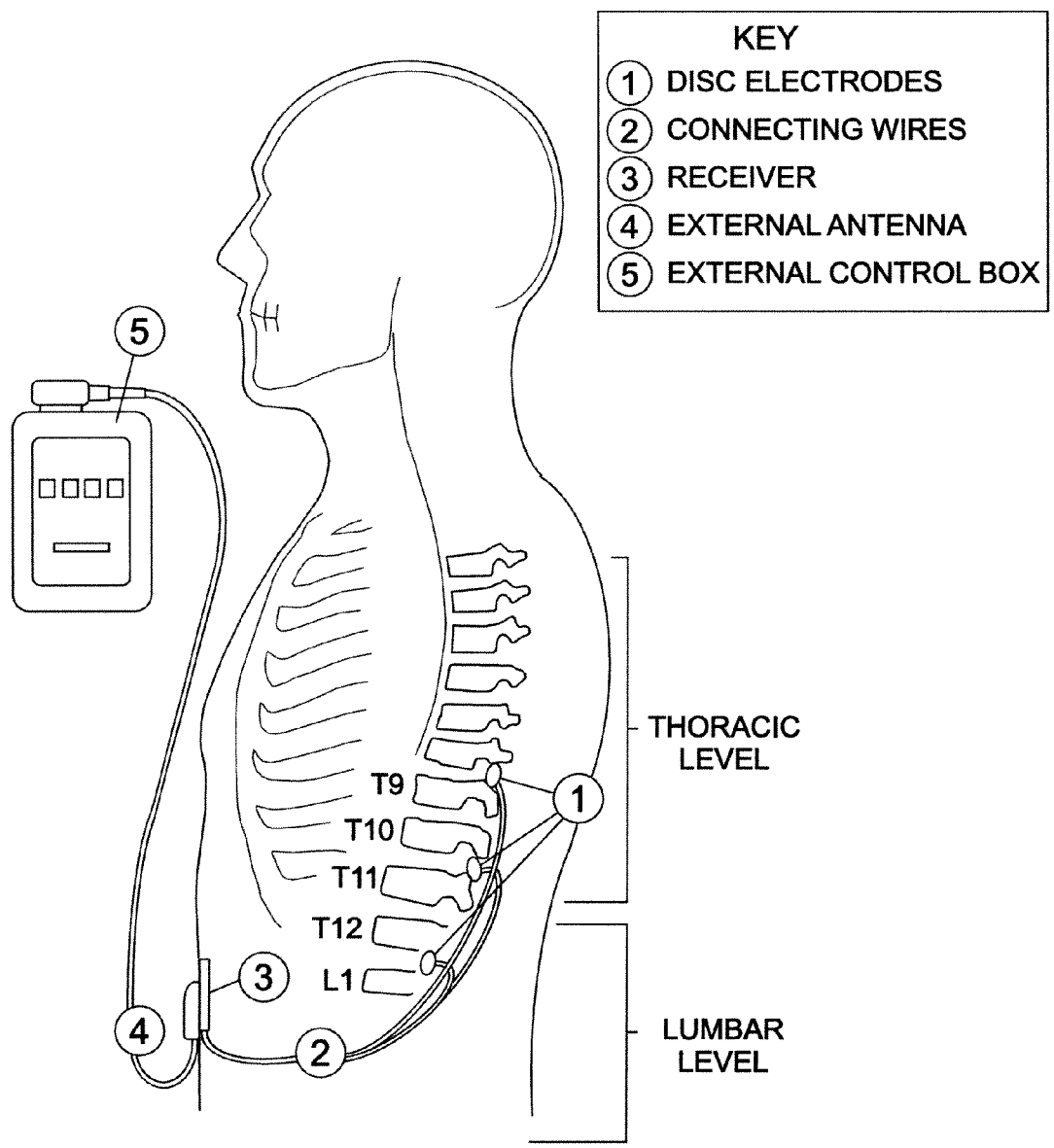
FIG. 7 is an illustration of a comparative example showing a human patient who has been implanted with disc electrodes instead of wire leads.

A single site pilot study was conducted to evaluate lower thoracic spinal cord stimulation (SCS) to restore an effective cough system in 11 tetraplegic subjects. A fully implantable electrical stimulation system was surgically placed in each subject; this system is depicted in FIG. 7. Partial hemi-laminectomies were required to place single-disc electrodes in the dorsal epidural space at the T9, T11 and L1 spinal levels. Three electrodes were placed (rather than two as in the animal studies) due to the greater length of the spinal cord in humans and the potential lack of spinal cord pathway activation. A radiofrequency receiver was also positioned in a subcutaneous pocket over the anterior chest wall. Electrode wires were tunneled subcutaneously and connected to the radiofrequency receiver. Stimulation was applied via an external antenna by activating a small portable external stimulus controller box powered by a rechargeable battery to each electrode lead alone and in combination.

Figure 8A:
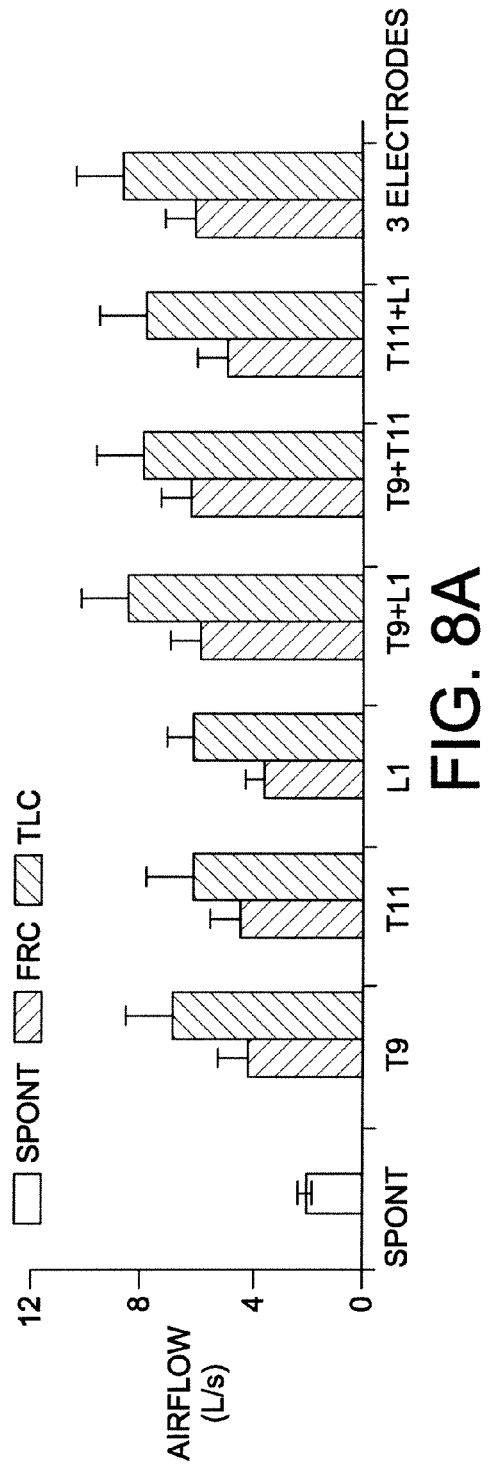
FIGS. 8A and 8B) showing the final results for patients implanted with disc electrodes utilizing unipolar stimulation.
Figure 8B:
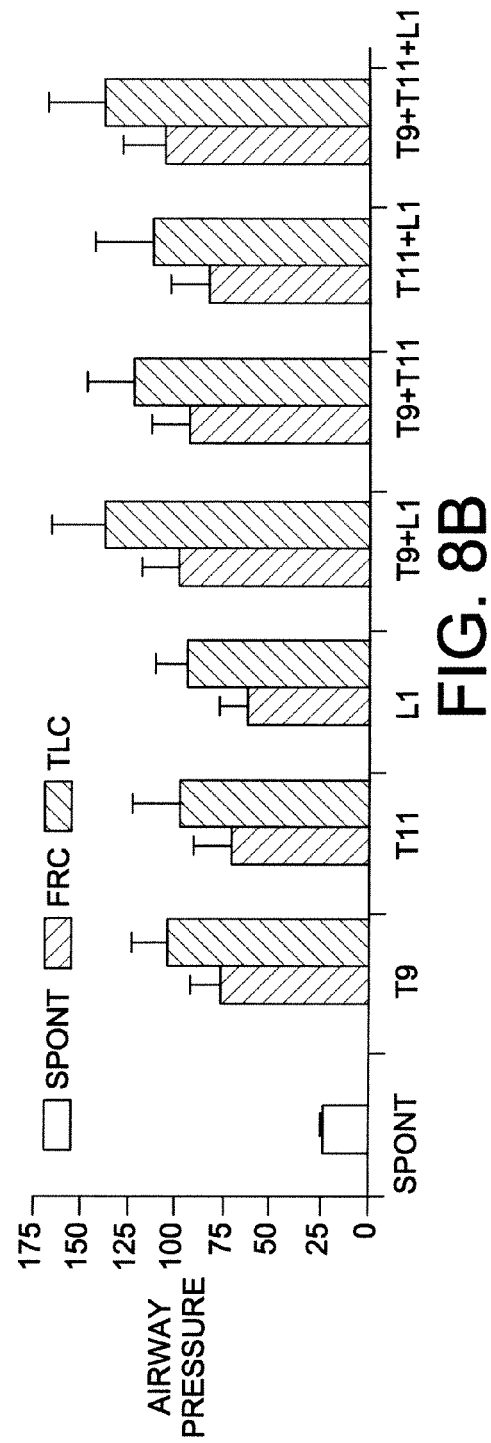

FIG. 8 shows the final results in nine of the initial 11 patients, who were each followed for a minimum of 12 months. In the graphs, "Spont" refers to spontaneous breathing, "FRC" refers to the functional residual capacity, and "TLC" refers to the total lung capacity. The results demonstrate that supramaximal SCS generates large positive airway pressures and high peak airflow rates during stimulation at each electrode. Maximum airway pressures and peak airflow rates were achieved with combined stimulation of any 2 electrodes. Like the animal studies results, only 2 electrodes were necessary to achieve maximum pressure generation. Unlike the animal studies, T9+T11 stimulation provided similar results to T9+L1 stimulation. At total lung capacity (TLC), mean maximum airway pressure generation and peak airflow rates were 130±30 cmH$_2$O and 8.6±1.8 Liters/second, respectively. Changes in airway pressure correlated closely with changes in peak flow rate during SCS, indicating that airway pressure generation was predictive of peak airflow rate development.

Importantly, repetitive stimulation every 30 seconds for 30 minutes did not result in the development of fatigue as pressure generation remained unchanged. This is an important finding since cough is often used repetitively over short time periods to expel secretions. SCS was performed at home by either the subjects themselves or caregivers 2-3 times/day on a chronic basis, and also as needed for secretion management.

The degree of difficulty in removing secretions improved markedly and the need for alternative methods of secretion removal were virtually eliminated. Subject life quality related to respiratory care also improved with subjects reporting greater control of their breathing problems. The incidence of pneumonia fell significantly from 1.7±0.5 to 0.2±0.1 events/subject year (p<0.01) and the mean level of trained caregiver support related to secretion management decreased from 16.9±7.9 times/week pre-implant to 2.9±1.2 times/week 40 weeks after implant. Subject mobility also increased significantly as many individuals no longer had to travel with trained caregivers and/or with any apparatus for suctioning. Three subjects developed mild hemodynamic effects associated with SCS which abated completely with chronic stimulation over 2-3 weeks. Some subjects experienced leg jerks during SCS which were generally well tolerated.

These preliminary results strongly suggest that an SCS cough system facilitates secretion management, reduces the need for caregiver support, reduces the incidence of respiratory tract infection and may reduce overall health care costs as well as improve the morbidity and mortality associated with respiratory complications in subjects with SCI.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method of electrically activating expiratory muscles of a patient to produce cough, comprising:
    applying bipolar stimulation using a first wire lead and a second wire lead to activate the expiratory muscles of the patient to produce cough;
    wherein the first wire lead and the second wire lead are located in a substantially parallel arrangement along a spinal cord of the patient, the first wire lead and the second wire lead each contain a first electrode and a second electrode, the first electrodes of the first wire lead and the second wire lead are located at a first spinal cord level, the second electrodes of the first wire lead and the second wire lead are located at a second spinal cord level, and during stimulation the first electrodes act as cathodes and the second electrodes act as anodes.

2. The method of claim 1, wherein the cathodes are closer to the brain of the patient than the anodes.

3. The method of claim 1, wherein bipolar stimulation is applied at a frequency of 10 Hz to 1000 Hz.

4. The method of claim 1, wherein bipolar stimulation is applied at a voltage of 10 V to 50 V.

5. The method of claim 1, wherein bipolar stimulation is applied at a pulse amplitude of 1 mA to 40 mA.

6. The method of claim 1, wherein bipolar stimulation is applied with a pulse width of 10 microseconds to 10 seconds.

7. The method of claim 1, wherein bipolar stimulation is applied at a maximum charge density of 1.0 microCoulombs/mm$^2$.

8. The method of claim 1, wherein bipolar stimulation is applied at a pulse amplitude of 10 mA to 40 mA; and a pulse width of 200 μsec to 400 μsec.

9. The method of claim 1, wherein the first wire lead and the second wire lead are located on a dorsal epidural surface of the spinal cord.

10. The method of claim 1, wherein the first wire lead and the second wire lead are located parallel to the midline of the patient.

11. The method of claim 1, wherein the first spinal cord level is the T9 spinal cord level and the second spinal cord level is the T11 spinal cord level.

12. The method of claim 1, wherein the first spinal cord level is the T11 spinal cord level and the second spinal cord level is the L1 spinal cord level.

13. The method of claim 1, wherein the first spinal cord level is the T9 spinal cord level and the second spinal cord level is the L1 spinal cord level.

14. A method of electrically activating expiratory muscles of a patient to produce cough, comprising:
    applying bipolar stimulation using a first wire lead and a second wire lead to activate the expiratory muscles of the patient to produce cough;
    wherein the first wire lead and the second wire lead are located in a substantially longitudinal arrangement along a spinal cord of the patient, the first wire lead and the second wire lead each contain a first electrode and a second electrode, the first electrode of the first wire lead is located at a first spinal cord level, the second electrode of the first wire lead is located at a second spinal cord level, the first electrode of the second wire lead is located at a third spinal cord level, and the second electrode of the second wire lead is located at a fourth spinal cord level;

wherein the first spinal cord level is different from the second spinal cord level, the third spinal cord level is different from the fourth spinal cord level, and the first spinal cord level is different from the fourth spinal cord level.

15. The method of claim 14, wherein the first electrode of the first wire lead acts as a cathode, the second electrode of the first wire lead acts as an anode, the first electrode of the second wire lead acts as a cathode, and the second electrode of the second wire lead acts as an anode.

16. The method of claim 14, wherein the first electrode of the first wire lead acts as a cathode and the second electrode of the second wire lead acts as an anode.

17. The method of claim 14, wherein bipolar stimulation is applied at a pulse amplitude of 1 mA to 40 mA.

18. The method of claim 14, wherein bipolar stimulation is applied at a maximum charge density of 1.0 microCoulombs/mm$^2$.

19. The method of claim 14, wherein the bipolar stimulation is applied at a pulse amplitude of 10 mA to 40 mA; and a pulse width of 200 μsec to 400 μsec.

20. The method of claim 14, wherein the first spinal cord level is the T9 spinal cord level, the second spinal cord level is the T11 spinal cord level, the third spinal cord level is the T11 spinal cord level, and the fourth spinal cord level is the L1 spinal cord level.

21. A method of electrically activating expiratory muscles in a patient to produce cough, comprising:

positioning a first wire lead and a second wire lead in a substantially parallel arrangement along a spinal cord and parallel to the midline of the patient, wherein the first wire lead and the second wire lead each contain a first electrode and a second electrode, the first electrodes of the first wire lead and the second wire lead are located at the T9 spinal cord level, the second electrodes of the first wire lead and the second wire lead are located at the T11 spinal cord level; and applying an effective amount of bipolar stimulation using the first wire lead and the second wire lead to activate the expiratory muscles of the patient to produce cough.

22. The method of claim 21, wherein the bipolar stimulation is applied at a frequency of 10 Hz to 1000 Hz.

23. The method of claim 21, wherein the bipolar stimulation is applied at a voltage of 10 V to 50 V.

24. The method of claim 21, wherein the bipolar stimulation is applied at a pulse amplitude of 1 mA to 40 mA.

25. The method of claim 21, wherein the bipolar stimulation is applied with a pulse width of 10 microseconds to 10 seconds.

26. The method of claim 21, wherein the bipolar stimulation is applied at a maximum charge density of 1.0 microCoulombs/mm$^2$.

27. The method of claim 22, wherein the bipolar stimulation is applied at a pulse amplitude of 10 mA to 40 mA; and a pulse width of 200 μsec to 400 μsec.

28. The method of claim 21, wherein the electrodes are located on a dorsal epidural surface of the spinal cord.

29. The method of claim 21, wherein the electrodes are located parallel to a midline of the patient.

* * * * *